United States Patent [19]
Daneman

[11] Patent Number: 5,409,451
[45] Date of Patent: Apr. 25, 1995

[54] WRIST BRACE
[75] Inventor: Alexis G. Daneman, Danville, Calif.
[73] Assignee: Orthopedic Technology, Inc., Tracy, Calif.
[21] Appl. No.: 78,685
[22] Filed: Jun. 16, 1993
[51] Int. Cl.[6] ............................................. A61F 5/00
[52] U.S. Cl. ...................................... 602/21; 602/20; 602/6
[58] Field of Search ...................... 602/20, 21, 22, 5, 6, 602/64

[56] References Cited
U.S. PATENT DOCUMENTS

| | | | |
|---|---|---|---|
| 3,788,307 | 1/1974 | Kistner | 602/21 |
| 3,938,509 | 2/1976 | Barber | 602/21 |
| 5,020,515 | 6/1991 | Mann et al. | 602/21 X |
| 5,058,576 | 10/1991 | Grim et al. | 602/21 |
| 5,205,812 | 4/1993 | Wasserman | 602/21 X |

OTHER PUBLICATIONS
Orthopaedic Appliances Atlas, vol. I, p. 305 (1952).
Zimmer Products (Encyclopedia of Products), 1978, p. 68.

*Primary Examiner*—Richard J. Apley
*Assistant Examiner*—Beverly A. Meindl
*Attorney, Agent, or Firm*—Townsend and Townsend Khourie and Crew

[57] ABSTRACT

A malleable, handed, wrist brace extending between the forearm and hand for immobilizing the wrist is disclosed. The brace includes a bendable and cut work hardened aluminum sheet cut with a central volar extension ending in a palmar support. The volar extension includes paired transversely extending forearm gripping arms and paired transversely extending wrist joint gripping arms. At the hand end of the brace, paired transversely extending palm gripping arms extend to opposite sides of the palm from just above the palmar support. The cut aluminum sheet has a molded exterior and liner interior bonded to opposite side with the gripper arms bent to confront the liner to the limb to be immobilized. The palmar support portion of the brace confronts a convex portion of the palmar support to the palm to provide preferred anatomical positioning of the hand with respect to the forearm (roughly 5° of dorsiflexion at the wrist). The brace is virtually self directing in its installation and requires minimum dexterity in such installation so that even a partially disabled user can install the disposable brace.

8 Claims, 2 Drawing Sheets

WRIST BRACE

This invention relates to a wrist brace. Specifically, a wrist brace is disclosed of the so-called "spoon type" for preventing dorsi-flexion and plantar flexion of the hand at the wrist. The brace has complete conformability to the wearer's forearm and wrist anatomy for immobilizing the wrist while permitting the maximum possible digital freedom of the braced wrist.

BACKGROUND OF THE INVENTION

Wrist injury is common. Frequently, and due to modern hand and digit tasks—such a typing—the hand in the vicinity of the carpal tunnel becomes irritated. As a result of such irritation, there is a need both to brace the hand away from plantar flexion and even to slight dorsi-flexion.

Prior art wrist braces are well known. Typically such braces include a spoon like member for supporting the hand. In such braces, the wrist is surrounded in the vicinity of the forearm over the radius and the ulna usually by a wrapping having multiple layers. A spoon like metal support has the longitudinal or handle portion of the spoon buried in between the layers of wrapping over the forearm. The spoon like member cantilevers out over the condyles of the radius and ulna with the convex side of the spoon member addressed to the palm of the hand. The convex portion of the spoon fits over the carpal tunnel in the vicinity of the carpal ligament. Thereafter, the hand is braced downward onto the convex surface of the spoon for support. Sufficient support is provided to prevent plantar flexion of the hand. At the same time the brace terminates both in the vicinity of the thumb and digits so that maximum digital freedom is preserved at the braced limb.

Such braces are usually custom made and formed of many layers. Further, they are held in place by installed tensile members such as laces or releasable fastening tape.

In the modern work place, injury or irritation in the area of the carpal tunnel is common. This area of the hand contains primarily the median nerve, flexor tendons and blood vessels surrounded by fluids. This area can be an area of chronic irritation requiring immobilization of the wrist—both at work and during sleeping hours. Braces are a form of non-surgical treatment used to sooth irritation in this area of the body.

SUMMARY OF THE INVENTION

A malleable, handed, wrist brace extending between the forearm and hand for immobilizing the wrist is disclosed. The brace includes a bendable and cut aluminum sheet having a central volar extension ending in a palmar support. The volar extension includes paired transversely extending forearm gripping arms and paired transversely extending wrist joint gripping arms. At the hand end of the brace, paired transversely extending palm gripping arms extend to opposite sides of the palm from just above the palmar support. The cut aluminum sheet has a molded exterior and liner interior bonded to the opposite side with the gripper arms bent to confront the liner to the limb to be immobilized.

The palmar support portion of the brace confronts a convex portion of the palmar support to the palm to provide preferred anatomical positioning of the hand with respect to the forearm (roughly 5° of dorsi-flexion at the wrist). The forearm gripping arms surround the forearm in gripping contact with the radial and ulnar aspects of the forearm. The wrist gripping arms are in contact with the radial and ulnar aspects of the carpal joints of the wrist, preferably just distal to carpal condyles. The palm gripping arms are bent to extend laterally around first and fifth meta-carpal bones, preferably extending to contact the dorsal hand.

With all gripper arms firmly in place, the longitudinal portion of the palmar support extends along and is supported from the volar aspect of the forearm to cantilever the convex side of palmar support in supporting relation to the palmar side of hand distal to the carpal bones and tunnel. The palmar gripper arms permit full flexion of digits including full opposition movement of the thumb as the thenar eminence is not encased by the brace. The upper limit of the palmar gripper arms permits normal flexion of the digits at the flexion lines of the palmar crease across the palm from the middle portion of the radial aspect of the fifth metacarpal to the distal ulnar aspect of the second metacarpal. The brace is virtually self directing in its installation and requires minimum dexterity in such installation so that even a partially disabled user can install the disposable brace.

DESCRIPTION OF THE PREFERRED EMBODIMENT

Figure 1:
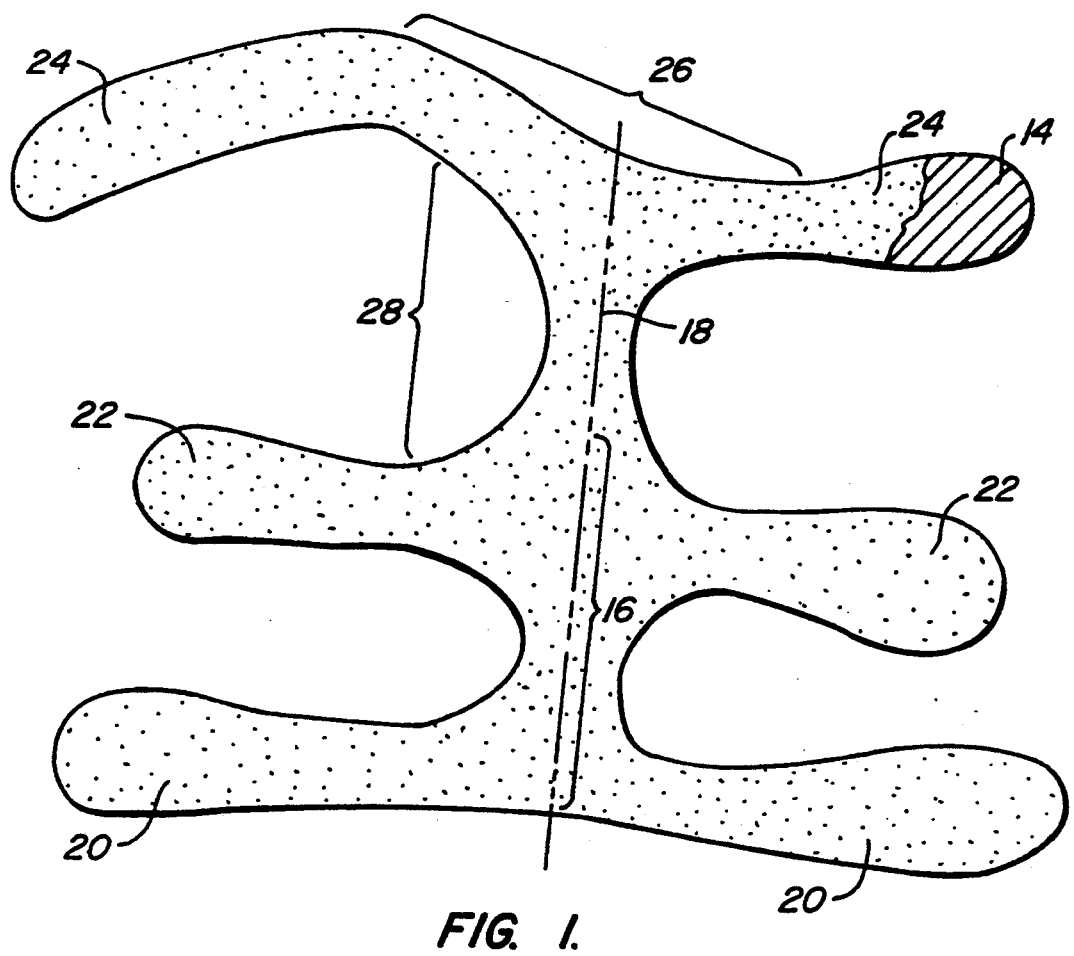
FIG. 1 is a plan view of the brace illustrating the central volar member terminating in the palmar support with the respective forearm gripper arms, wrist gripper arms, and palm gripper arms in a flat disposition.

Referring to FIG. 1, the malleable, handed, wrist brace extending between the forearm and hand for immobilizing the wrist is disclosed. The brace includes a bendable and cut aluminum sheet 14 cut with a central volar extension 16 ending in a palmar support 18. The volar extension includes paired transversely extending forearm gripping arms 20 and paired transversely extending wrist joint gripping arms 22.

At the hand end of the brace, paired transversely extending palm gripping arms 24 extend to opposite sides of the palm from just above the palmar support. The cut aluminum sheet has a molded exterior 30 (See FIGS. 2 and 3) and liner interior 24 (See FIG. 1) bonded to opposite side. It will be understood that the brace is usually made with four different sizes—small, medium, large and extra large—with pediatric sizes possible. Further, the brace is "handed", with the right hand brace here being shown. It will be understood that by merely reversing the sides of the cut aluminum to which the molded exterior 30 and liner 24 are fastened, the opposite left handed brace may be made.

The upper portion of the brace terminates with a palmar crease portion 26. The position of this palmar crease portion 26 permits full movement of the digits when the brace is worn. Similarly, thenar eminence border 28 permits the hand adjacent the thumb maximum flexibility in enabling confrontation of the thumb with the other digits of the hand while the brace is worn.

Figure 2:
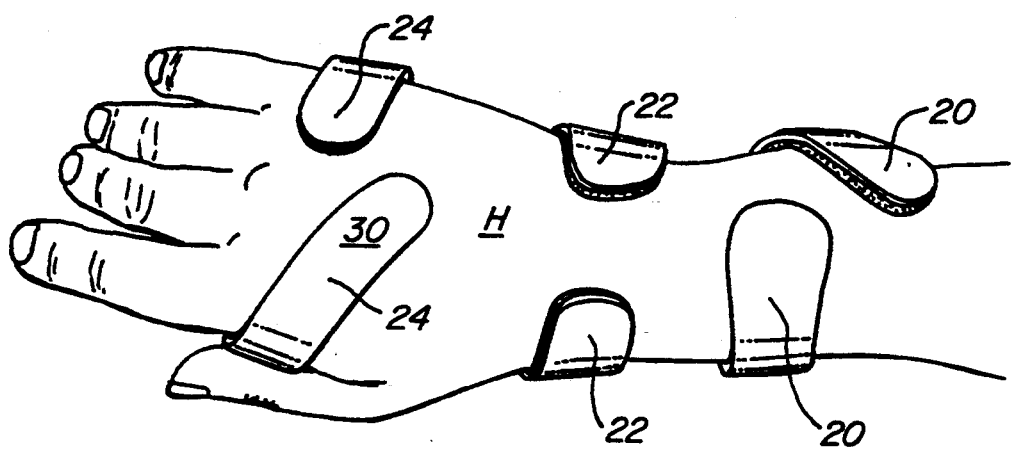
FIG. 2 is a top plan view of the brace affixed to a forearm illustrating the gripper arms affixed to the dorsal aspect of the hand and forearm; and, FIG. 3 is a bottom perspective view of the brace affixed to a forearm illustrating the gripper arms affixed to the volar aspect of the hand and forearm with the brace depressing the palmar portion of the hand for support.
Figure 3:
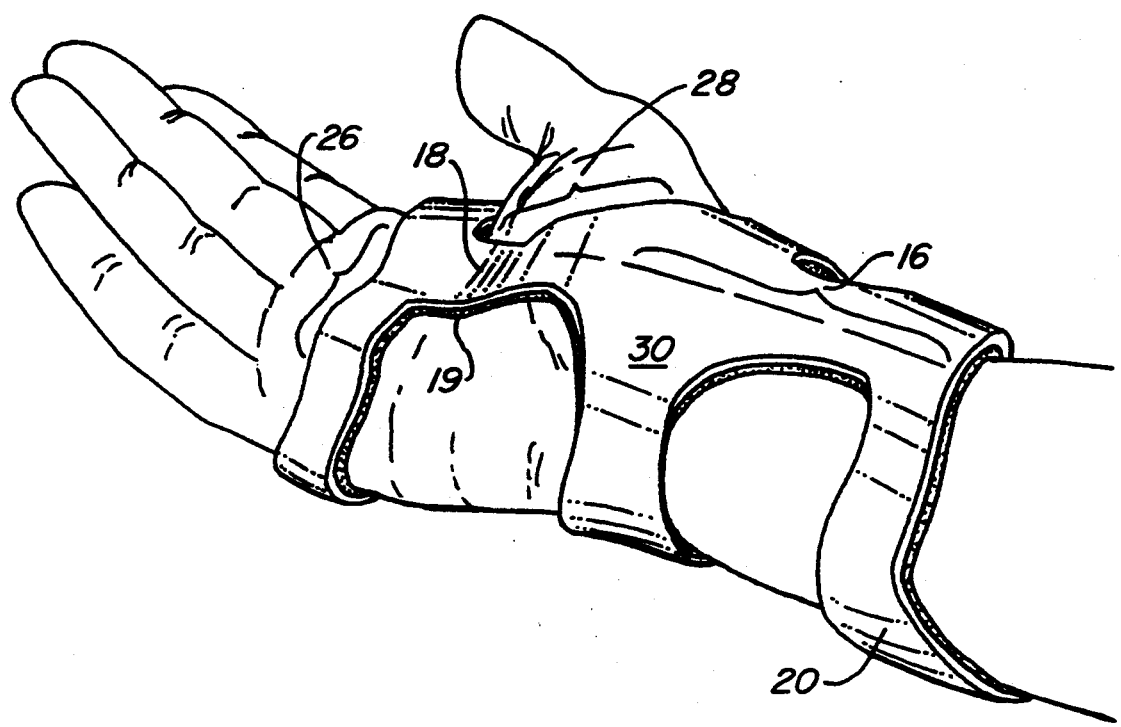

FIG. 2 & 3 show how the brace is worn. Gripper arms 20, 22, and 24 are bent to confront the liner to the limb to be immobilized, here right hand H. The palmar support portion 18 of the brace confronts a convex portion 19 of the palmar support to the palm to provide preferred anatomical positioning of the hand to the forearm (roughly 5° of dorsi-flexion at the wrist). The forearm gripping arms 20 surround the forearm in gripping contact with radial and ulnar aspects of the forearm. The wrist gripping arms 22 are in contact with radial and ulnar aspects of the carpal joints of the wrist, preferably just distal to the carpal condyles. The palm gripping arms 24 are bent to extend laterally around first and fifth meta-carpal bones preferably extending to contact the dorsal hand.

With all gripper arms 20, 22, and 24 firmly in place, the longitudinal portion of palmar support extends along and is supported from the volar aspect of the forearm to cantilever the convex side of palmar support 18 in supporting relation to palmar side of hand distal to carpal bones and tunnel. The palmar gripper arms terminating at palmar crease portion 26 permit full flexion of digits including full opposition movement of the thumb as the thenar eminence is not encased by border 28 of the brace. The upper limit 26 of the palmar gripper arms permits normal flexion of the digits such as along the flexion lines of the palmar crease across the palm from the middle portion of the radial aspect of the fifth metacarpal to the distal ulnar aspect of the second metacarpal.

It should be noted that the brace is virtually self directing in its installation and requires minimum dexterity in such installation so that even a partially disabled user can install the disposable brace.

What is claimed is:

1. A malleable, handed, single, unitary, wrist brace extending between the forearm and hand for immobilizing the wrist consisting of:
    a bendable and cut sheet having
        a central volar extension ending in a palmar support;
        paired transversely extending forearm gripping arms extending from the forearm extremity of said brace;
        paired transversely extending wrist joint gripping arms extending from a medial portion of said brace;
        paired transversely extending palm gripping arms extending to opposite sides of the palm from just above the palmar support; and,
    a molded exterior on one side of said cut sheet and liner interiorly bonded to opposite side of said sheet.

2. The malleable, handed, wrist brace extending between the forearm and hand for immobilizing the wrist according to claim 1 and wherein:
    said sheet is formed of aluminum.

3. The malleable, handed, wrist brace extending between the forearm and hand for immobilizing the wrist according to claim 1 and wherein:
    said sheet is co-extensive with said molded exterior.

4. A process of immobilizing the wrist between the hand a forearm with a malleable, handed, wrist brace extending between the forearm and hand comprising the steps of:
    providing a single, unitary, bendable and cut sheet consisting of:
        a central extension ending in a palmar support;
        paired transversely extending forearm gripping arms extending from the forearm extremity of said brace;
        paired transversely extending wrist joint gripping arms extending from a medial portion of said brace;
        paired transversely extending palm gripping arms extending to opposite sides of the palm from just above the palmar support;
        a molded exterior on one side of said cut sheet and liner interiorly bonded to opposite side of said sheet;
    bending the palmar support portion of the brace to a convex portion to form a palmar support;
    bending and wrapping the forearm gripping arms surround the forearm in gripping contact with radial and ulnar aspects of the forearm;
    bending and wrapping the wrist gripping arms to provide contact with radial and ulnar aspects of the carpal joints of the wrist preferably just distal to carpal condyles; and,
    bending and wrapping the palm gripping arms to extend laterally around the first and fifth meta-carpal bones and extending to contact the dorsal hand whereby said wrist is immobilized.

5. The process of immobilizing the wrist between the hand a forearm with a malleable, handed, wrist brace extending between the forearm and hand of claim 4 including the steps of:
    bending said volar central volar extension to dispose the palmar support to provide anatomical positioning of the hand to the forearm at about 5° of dorsi-flexion at the wrist.

6. The process of immobilizing the wrist between the hand and forearm with a malleable, handed, wrist brace extending between the forearm and hand of claim 4 including the steps of:
    placing the longitudinal portion of the palmar support along the volar aspect of the forearm to cantilever the convex side of the palmar support in supporting relation to the palmar side of the hand distal to the carpal bones and tunnel.

7. The process of immobilizing the wrist between the hand and forearm with a malleable, handed, wrist brace extending between the forearm and hand of claim 4 including the steps of:
    forming the palmar gripper arms to permit full flexion of digits including full opposition movement of the thumb with the thenar eminence not encased by the brace.

8. The process of immobilizing the wrist between the hand a forearm with a malleable, handed, wrist brace extending between the forearm and hand of claim 4 including the steps of:
    forming the upper limit of the palmar gripper arms to permit normal flexion of the digits at the flexion lines of the palmar crease across the palm from the middle portion of the radial aspect of the fifth metacarpal to the distal ulnar aspect of the second metacarpal.

* * * * *